United States Patent [19]
Brimhall

[11] Patent Number: 5,304,144
[45] Date of Patent: Apr. 19, 1994

[54] CATHETER INTRODUCER WITH ENHANCED NEEDLE GRIPPING

[75] Inventor: Greg L. Brimhall, West Jordan, Utah

[73] Assignee: Becton, Dickinson and Company, Franklin Lakes, N.J.

[21] Appl. No.: 32,948

[22] Filed: Mar. 17, 1993

[51] Int. Cl.⁵ .................................... A61M 5/00
[52] U.S. Cl. ................... 604/177; 604/165; 604/171
[58] Field of Search ........... 604/164, 165, 171, 177, 604/168; 128/DIG. 26, 900

[56] References Cited

U.S. PATENT DOCUMENTS

| | | | |
|---|---|---|---|
| 4,177,809 | 12/1979 | Moorehead | 128/214.4 |
| 4,362,156 | 12/1982 | Feller, Jr. et al. | 604/165 |
| 4,834,708 | 5/1989 | Pillari | 604/165 |
| 4,941,881 | 7/1990 | Masters et al. | 604/162 |
| 4,969,876 | 11/1990 | Patterson | 604/171 |
| 5,061,250 | 10/1991 | Shields | 604/198 |
| 5,108,376 | 4/1992 | Bonaldo | 604/177 |
| 5,147,319 | 9/1992 | Ishikawa et al. | 604/174 |
| 5,149,328 | 9/1992 | Zaha | 604/177 |
| 5,163,913 | 11/1992 | Rantanen-Lee et al. | 604/177 |

*Primary Examiner*—John G. Weiss
*Attorney, Agent, or Firm*—Michael G. Schwarz

[57] ABSTRACT

A catheter introducer set is disclosed. The device comprises a cannula for insertion into a blood vessel, a tube in fluid communication with the cannula and a needle for assisting in the introduction of the cannula into the vessel. Between the cannula and the tube is an intermediate member which allows the needle to be gripped so that it can be inserted into the blood vessel. The intermediate member preferably has a pair of wings to facilitate the gripping of the needle. The needle has an opening or openings in it to allow a user to observe blood flashback during insertion of the needle into the blood vessel. The intermediate member is made of polyurethane and is provided with a groove to facilitate the gripping of the needle. The wings have ramps on them to facilitate the gripping of the needle. Ribs are also provided between the ramp and the intermediate member to facilitate gripping. The wings describe an angle of less than 180 degrees.

19 Claims, 4 Drawing Sheets

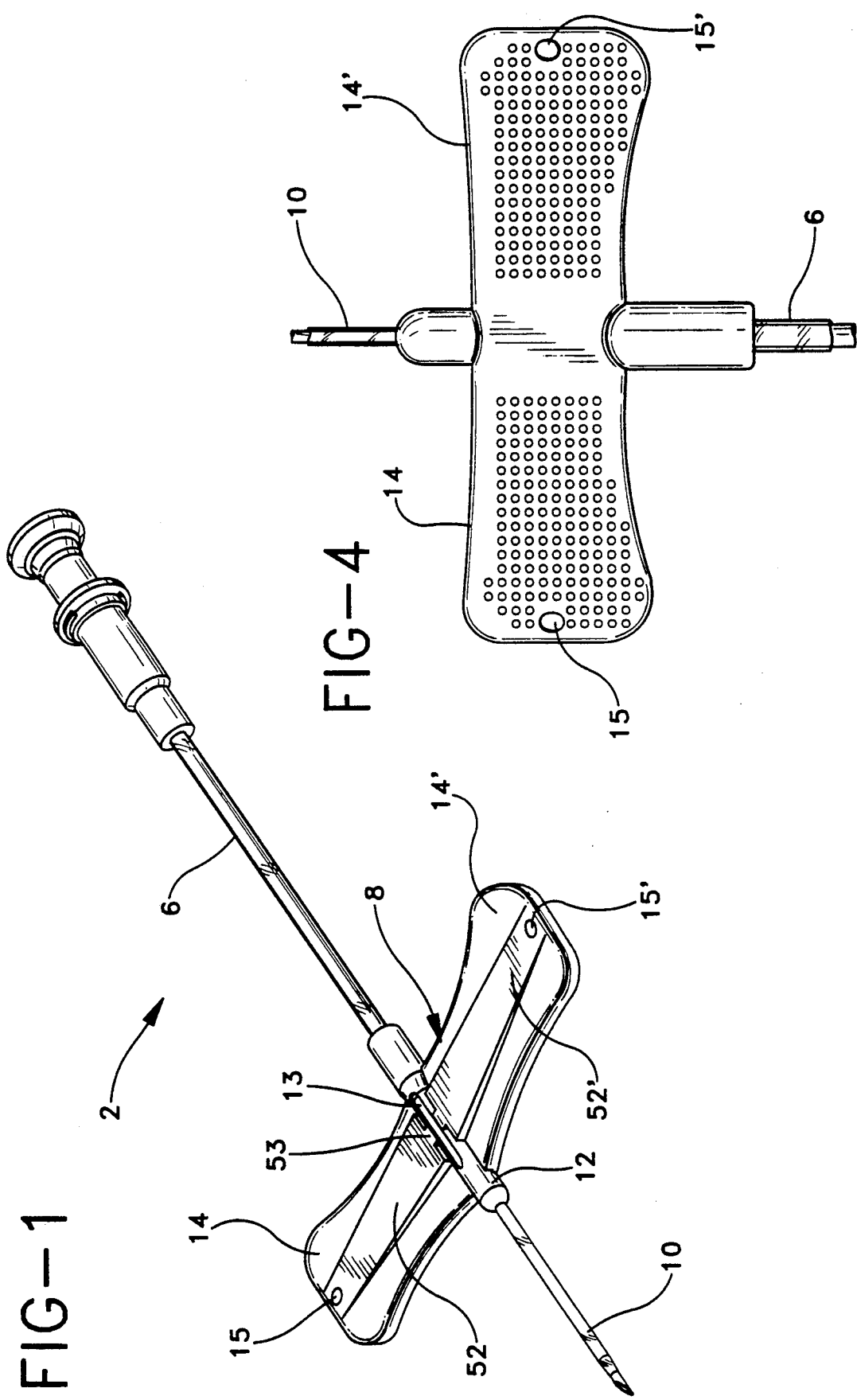

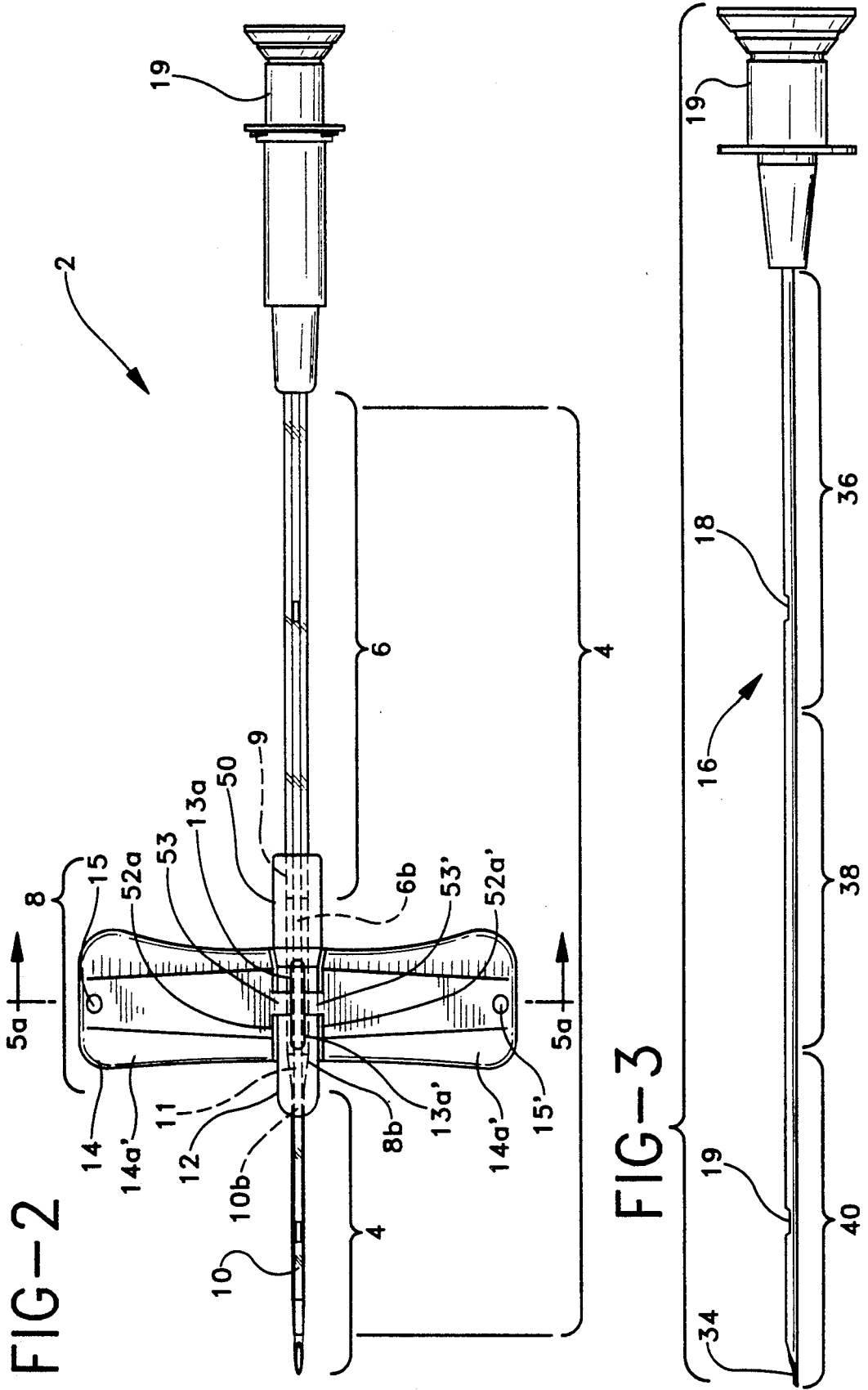

CATHETER INTRODUCER WITH ENHANCED NEEDLE GRIPPING

BACKGROUND

The present invention relates generally to the field of medical catheters. In particular it relates to a catheter for providing access to a blood vessel and the like and having features which facilitate its introduction into the vessel.

Winged infusion sets are commonly used by the medical profession for the infusion of medication and the drawing of fluids from vessels. A species of such devices (a "scalp vein set") may comprise a needle with wings attached to it. Attached to the needle, and in fluid communication with the needle bore is a translucent tube through which medication can be infused or fluids drawn. Another species (a winged catheter introducer), comprises a flexible cannula attached to a winged member and a translucent tube. Inside the cannula is a needle with a wire attached to it. The needle aids in the insertion of the catheter into a vessel and is withdrawn by pulling the wire once the cannula has been successfully introduced into the vessel.

Such devices are introduced into the vessel as follows: The wings are gripped between the practitioner's forefinger and thumb. The practitioner uses the needle to pierce the skin in the vicinity of the vessel to be accessed. When the vessel is penetrated, the pressure in the vessel will cause blood to flow up the needle bore and into the translucent tubing. The practitioner verifies the penetration of the vessel by looking for blood "flashback" in the tubing. Once the device is satisfactorily positioned in the vessel it may be left there for some time. In the case of a winged catheter introducer, the needle is withdrawn from the cannula.

A device of the second species is shown in U.S. Pat. Nos. 4,177,809 and 5,163,913, which are incorporated herein by reference. Such devices are sold under the trademarks Intima ™ and Angioset ® by Becton Dickinson & Co. of Franklin Lakes, N.J.

SUMMARY OF THE INVENTION

The invention is a catheter introducer set by means of which the catheter is introduced into a blood vessel or the like by means of an introducer needle as described in the Background section above. The introducer set has enhanced needle gripping features.

The preferred embodiment of the invention may be summarized as follows: The catheter introducer set comprises a tube having a first lumen. A cannula having a first end for introducing into a blood vessel and a second end is provided. The cannula comprises a second lumen between the first and second ends. The second internal lumen is in fluid communication with the first lumen. Linking the cannula and the tube is an intermediate member. The intermediate member is radially elastically deformable.

A needle comprising a sharp tip is disposable lengthwise in the lumen of the cannula such that at least part of the needle lies within the intermediate member. Gripping means are provided for squeezing the intermediate member such that the part of the needle lying within the intermediate member can be gripped by the intermediate member. The intermediate member is provided with an elongate indentation substantially parallel to the lumen of the cannula to faciliate gripping of the needle by the intermediate member.

Preferably the gripping means comprises a pair of wings attached to the intermediate member. Each wing is substantially on an opposite side of the intermediate member to the other wing and the wings are adapted to squeeze the intermediate member by bringing the wings towards each other. The wings have surfaces having generally wedge-shaped members on them. The generally wedge-shaped members assist in squeezing the intermediate member.

In a further preferred embodiment, the squeezing of the intermediate member is enhanced by the provision of ribs projecting from the generally wedge-shaped members towards the intermediate member.

The intermediate member is made of polyurethane.

BRIEF DESCRIPTION OF THE DRAWINGS

FIG. 1 is a perspective view of the invention;
FIG. 2 is a plan view of the invention;
FIG. 3 is side view of the needle of the invention;
FIG. 4 is a reverse plan view of the intermediate member of the invention.

Figure 5:
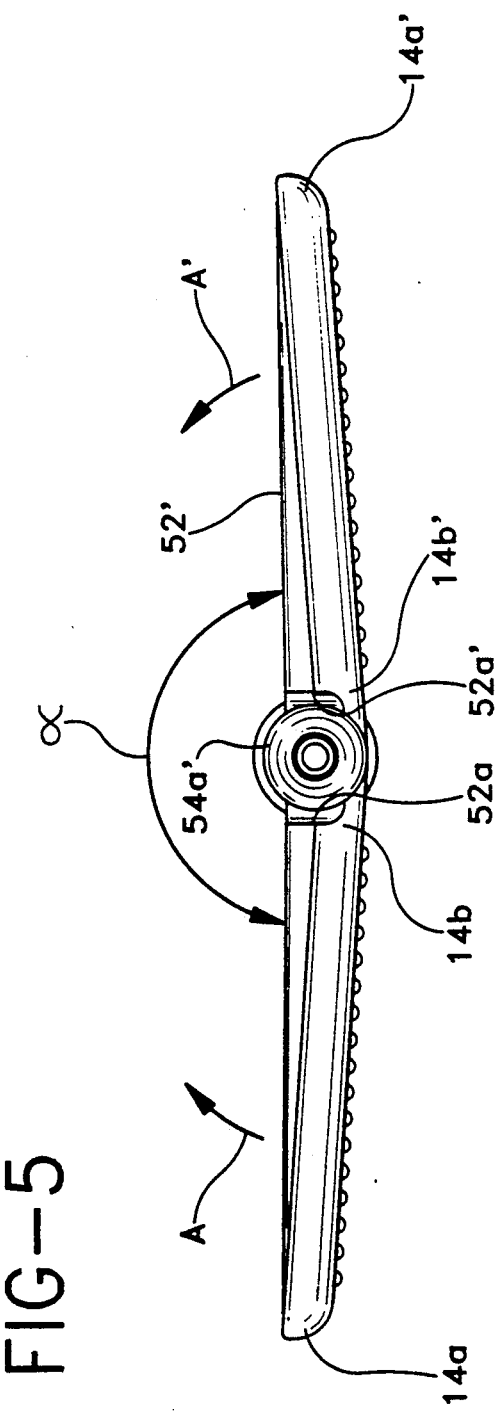
FIG. 5 is a front view of the invention.

Shown in FIG. 1 is the catheter introducer set 2 of the present invention. Catheter introducer set 2 is made up of a hollow elongate member 4 which is in turn made up of three members: first tube 6, cannula 10 and intermediate member 8. During normal use, first tube 6 is proximal to the medical practitioner or nurse and cannula 10 is distal of the practitioner or nurse. First tube 6 is made of a transparent medical grade flexible polyvinyl chloride tubing having a durometer hardness in a range of approximately 60–80 Shore A and available from Natvar Company. Preferably Natvar 660 having a hardness of 70 Shore A is used. First tube 6 is insert molded to intermediate member 8 as indicated by dotted area 9 (see FIG. 2). Intermediate member 8 is molded from polyurethane having a durometer hardness of approximately 80 Shore A. Such material is available from Dow Chemicals under the name Pellethane ® 2363-80A. Intermediate member may be made of polyurethane having a durometer hardness in a range of approximately 60 to 95 Shore A. The precise durometer hardness of the polyurethane is not crucial.

The choice of the polyurethane material described above provides certain benefits. Among other advantages discussed herein, it provides good bond strength between the intermediate member 8 and first tube 6 and cannula 10, thus making insert molding of the device feasible. It also provides cost savings over materials of the prior art.

Intermediate member 8 includes a substantially cylindrical section 12. Attached to the substantially cylindrical section 12 is a pair of wings 14, 14', the function of which will be described presently. First tube 6 and cannula 10 respectively have bores 6b and 10b which are in fluid communication (via bore 8b of intermediate member 8) and generally coaxial with each other. The term "bore" is taken to encompass a lumen.

Attached to intermediate member 8 by insert molding is cannula 10. Cannula 10 is an intravenous catheter tube preferably made of a polyurethane material and tip configuration as described in U.S. Pat. No. 4,588,398 which is incorporated herein by reference. The catheter tube is intended for insertion into a patient's blood vessel. Alternatively second member many be made of Teflon ®. Proximal end 11 of second member 10 (indicated by dotted line in FIG. 2) is partially covered by cylindrical section 12.

Figure 5A:
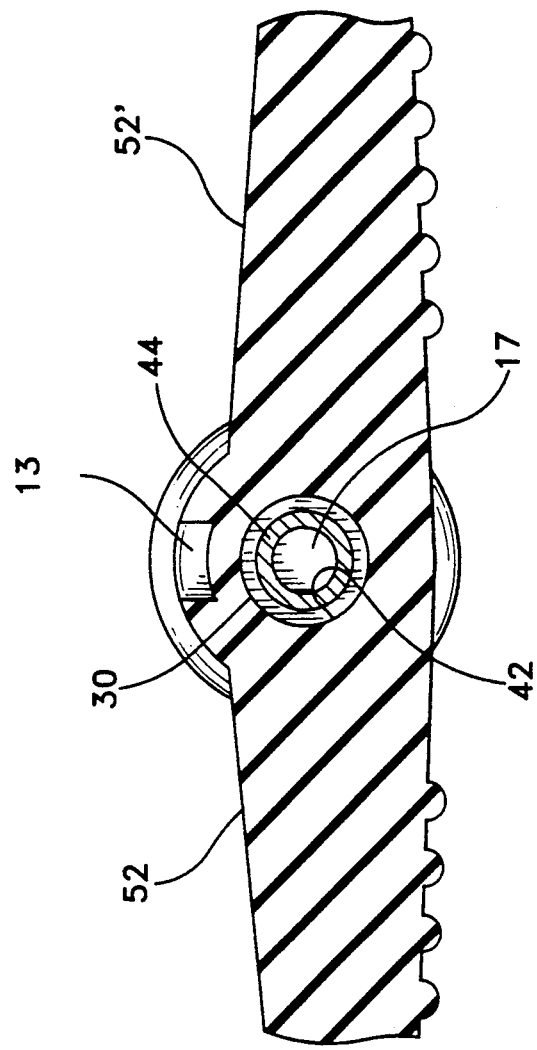
FIG. 5a is a sectional view through section 5a—5a' of FIG. 2; and,
FIG. 6 is a detailed sectional view through section 5a—5a'.

Needle 16 is slidably mounted in bores 6b, 8b and 10b. Needle 16 itself has lumen 17 defined by cylindrical wall 44 (see FIG. 5a). When needle 16 lies in bores 6b, 8b and 10b, an annular space 30 is formed between bores 6b, 8b and 10b and cylindrical wall 44 of needle 16. Needle 16 has a sharpened end 34 for piercing the skin and a blood vessel of a patient to assist in the introduction of at least part of second member 10 into the vessel. At the end of needle 16 opposite to sharp end 34 finger grip 19 is provided to assist in the manipulation of needle 16.

As shown in FIG. 3, needle 16 is conceptually divided into regions 36, 38 and 40 which respectively spatially correspond to first, intermediate and second members 6, 8 and 10 of hollow elongate member 4 when needle 16 is placed longitudinally in bores 6b and 10b. This is shown by the juxtaposition of FIGS. 2 and 3.

In region 36 wall 44 is provided with a first notch-like opening 18 which permits fluid to flow from lumen 17 into annular space 30 when needle 16 is placed lengthwise in hollow elongate member 4. Located in region 40 is a second notch-like opening 19 in wall 44 which also permits fluid to flow from lumen 17 into annular space 30 when needle 16 is in hollow elongate member 4.

Wings 14, 14' and intermediate member 8 will now be described in greater detail. Intermediate member 8 is made up of substantially cylindrical member 12 with a portion of enlarged diameter 50 for accommodating first member 6 which is insert molded into substantially cylindrical member 12.

Wings 14, 14' are integrally molded with intermediate member 8 and are oriented at an angle α to each other. Wings 14, 14' are respectively substantially on opposite sides of intermediate member 8. Angle α is approximately 170 degrees. The purpose of choosing α to be less than 180 degrees is to provide an incentive for the user to grip wings 14, 14' and bring them together in the direction indicated by arrows A and A'. As will be seen, it is important to the proper operation of the device that wings 14, 14' be bent in the right direction. The "prebend" of angle α assists in ensuring that the nurse or practitioner bends the wings in the direction of arrows A, A'.

Figure 6:
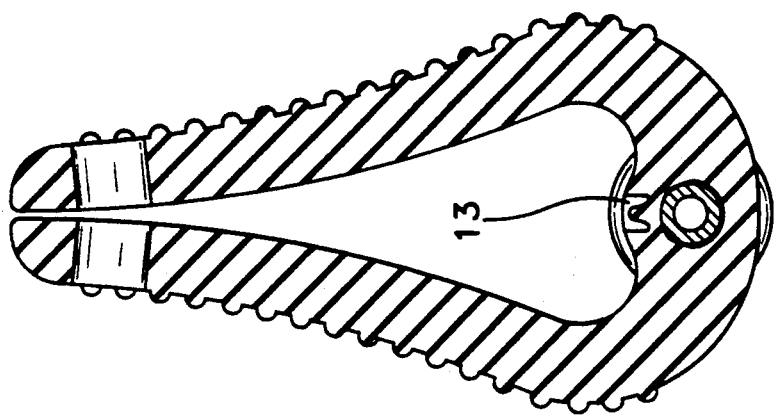

Wings 14, 14' have surfaces 14a, 14a' which are provided with generally wedge-shaped ramps 52, 52' which have surfaces 52a, 52a' adjacent substantially cylindrical member 12. Ramps 52, 52' slope upwards from the outer ends 14a, 14a' of wings 14, 14' to the inner ends 14b, 14b' of wings 14, 14' which are adjacent substantially cylindrical member 12. When wings 14, 14' are brought towards each other in the direction of arrows A, A', as shown in FIG. 6 surfaces 52a, 52a' touch outer walls 54a, 54a' of substantially cylindrical member 12. Further bending of wings 14, 14' in the direction of arrows A, A' causes ramps 52, 52' to squeeze substantially cylindrical member 12. The squeezing of member 12 causes inner surface 42 of intermediate member 8 to touch and thus grip needle 16.

The gripping of needle 16 is enhanced by the provision of slot 13 in member 12. Slot 13 is molded into member 8. The effect of slot 13 is to provide an area of member 12 with a reduced wall thickness which facilitates the squeezing of member 12. This enhanced squeezing causes needle 16 to be gripped more effectively than it would be in the absence of slot 13. The gripping of needle 16 is shown more clearly in FIGS. 6 and 6a. In FIG. 6 is can be seen that slot distorts when wings 14, 14' are brought towards each other in the direction of arrows A, A'. This phenomenon is more clearly seen in FIG. 6a which also shows the gripping of needle 16 by inner surface 42.

To enhance the gripping of needle 16 further, ramps 52, 52' are provided with ribs 53, 53' which lie between surfaces 52a and outer wall 12a of member 12. Ribs 53, 53' are integrally molded with member 12. They extend from surfaces 52a, 52a' towards slot 13, terminating at walls 13a, 13a' of slot 13. Ribs 53, 53' assist in the squeezing of member 12 by transmitting force from surfaces 52a, 52a' to walls 13a, 13a' of slot 13. It will be recognized that intermediate member will not effectively grip needle 16 if wings 14, 14' are not bent in the direction of arrows A, A'.

In addition to the improved gripping provided by the geometry described above, gripping of the needle is further enhanced by the choice of the material of intermediate member 8. The polyurethane described above has properties of "stickiness" which improve the grip between needle 16 and inner surface 42 of intermediate member 10. Using that material obviates the need to roughen needle wall 44 to enhance gripping.

Needle 16 assists in the introduction of the catheter tube of second member 10 into a blood vessel. Sharp end 34 pierces the skin and the vessel to make a puncture hole through which catheter tube 10 can enter the vessel. Since catheter tube 10 is made of a soft material, it needs the assistance of needle 16 if it is to be introduced into the vessel. The gripping of needle 16 by wings 14, 14a' enables catheter tube 10 to be held relative to needle 16 and hence enables it to be introduced into the vessel when needle 16 penetrates the vessel. In order to avoid damaging the vessel, needle 16 is withdrawn from the vessel and the soft catheter tube 10 remains. Needle 16 is withdrawn by simply releasing wings 14, 14' so that surfaces 52a, 52a' no longer grip substantially cylindrical member 12 and hence needle 16. Once wings are released, needle 16 is withdrawn by pulling finger grip 19. Wings 14, 14' can be used to secure the device to the skin of the patient by taping or suturing wings to the skin. Suture holes 15, 15' are provided on wings 14, 14' to facilitate suturing.

Figure 6A:
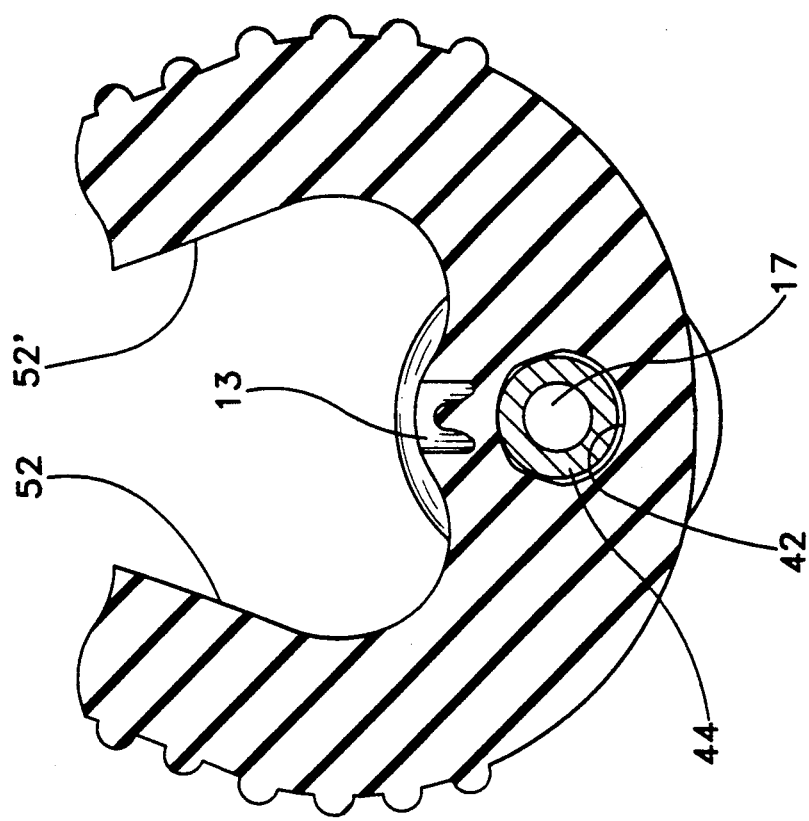

It will be noted that when needle 16 is gripped the annular space 30 which is between substantially cylindrical member 12 and needle 16 is constricted (see FIG. 6a). Thus, fluid flow in annular space 30 is inhibited. In order to determine whether needle 16 has penetrated a blood vessel as opposed to muscle or other tissue, it is necessary to observe whether blood has entered lumen 17 of needle 16 when needle 16 is inserted into the patient. The blood pressure in the vessel will cause blood to be forced up lumen 17 of needle 16 if needle 16 penetrates a blood vessel. If no blood or a very small amount has entered lumen 17, it is unlikely that a vessel has been pierced. If blood enters lumen 17, the vessel has probably been penetrated. Thus it is necessary to provide means for observing blood entering needle 16. When needle 16 penetrates the vessel, blood will flow through first opening 19 and into annular space 30. Since annular space 30 is constricted during insertion of needle 16 into the vessel due to the bending of wings 14, 14', blood cannot be observed flowing though annular space 30 from second member 10 into first member 6. To solve this problem, second opening 18 is provided in first region 36. Second opening 18 provides a fluid path from lumen 17 of needle 16 to annular space 30 in the vicinity of member 6. Thus, on penetration of the vessel by needle 16, blood is able to flow up lumen 17 and through openings 18 and 19. Blood can be observed in tube 6 because it is translucent.

The foregoing description is of the preferred embodiment of the invention. It is intended to exemplify the invention and not to limit it. The scope of the invention is to be determined by the appended claims and their equivalents.

I claim:

1. A catheter introducer set comprising:
   a tube having a first internal lumen;
   a cannula having a first end for introducing into a blood vessel and a second end, the cannula having a second internal lumen between the first and second ends;
   an intermediate member linking the cannula and the tube, the intermediate member comprising a generally cylindrical section, the generally cylindrical section being radially elastically deformable;
   a needle comprising a sharp tip, the needle being disposable lengthwide in the first and second lumens such that at least part of the needle lies within the intermediate member;
   gripping means for squeezing the intermediate member such that the part of the needle lying within the intermediate member can be gripped by the intermediate member;
   wherein the intermediate member is provided with an elongate indentation in the generally cylindrical section, the indentation being substantially parallel to the lumen of the cannula to facilitate gripping of the needle by the intermediate member.

2. The catheter introducer set of claim 1 wherein the gripping means comprises a pair of wings attached to the intermediate member, wherein each wing is substantially on an opposite side of the intermediate member to the other wing, and wherein the wings are adapted to squeeze the intermediate member by bringing the wings towards each other.

3. The catheter introducer set of claim 2 wherein the wings comprise surfaces having generally wedge-shaped members thereon, the generally wedge-shaped members comprising means for squeezing the intermediate member.

4. The catheter introducer set of claim 3 wherein the means for squeezing comprise ribs projecting from the generally wedge-shaped members towards the intermediate member.

5. The catheter introducer set of claim 1 wherein the intermediate member is made of polyurethane.

6. The catheter introducer set of claim 5 wherein the polyurethane has a durometer hardness in a range of approximately 60 to 95 Shore A.

7. The catheter introducer set of claim 5 wherein the polyurethane has a durometer hardness of approximately 80 Shore A.

8. The catheter introducer set of claim 5 wherein the tube is made of polyvinyl chloride.

9. The catheter introducer set of claim 8 wherein the polyvinyl chloride has a durometer hardness in a range of approximately 60 to 80 Shore A.

10. The catheter introducer set of claim 9 wherein the polyvinyl chloride has a durometer hardness of approximately 70 Shore A.

11. A catheter introducer set comprising:
    a tube having a first internal lumen;
    a cannula having a first end for introducing into a blood vessel and a second end, the cannula having a second internal lumen between the first and second ends;
    an intermediate member linking the cannula and the tube, the intermediate member comprising a generally cylindrical section, the generally cylindrical section being radially elastically deformable;
    a needle comprising a sharp tip, the needle being disposed lengthwise in the first and second lumens such that at least part of the needle lies within the intermediate member;
    gripping means for squeezing the intermediate member such that the part of the needle lying within the intermediate member can be gripped by the intermediate member, the gripping means comprising a pair of wings attached to the intermediate member, each wing being substantially on an opposite side of the intermediate member to the other wing, the wings being adapted to squeeze the intermediate member by bringing the wings towards each other.
    wherein the generally cylindrical section is provided with an elongate indentation substantially parallel to the lumen of the cannula to facilitate gripping of the needle by the intermediate member.

12. The catheter introducer set of claim 11 wherein the wings comprise surfaces having generally wedge-shaped members thereon, the generally wedge-shaped members comprising means for squeezing the intermediate member.

13. The catheter introducer set of claim 12 wherein the means for squeezing comprise ribs projecting from the generally wedge-shaped members towards the indentation in the winged member.

14. The catheter introducer set of claim 11 wherein the intermediate member is made of polyurethane.

15. The catheter introducer set of claim 14 wherein the polyurethane has a durometer hardness in a range of approximately 60 to 95 Shore A.

16. The catheter introducer set of claim 14 wherein the polyurethane has a durometer hardness of approximately 80 Shore A.

17. The catheter introducer set of claim 14 wherein the tube is made of polyvinyl chloride.

18. The catheter introducer set of claim 17 wherein the polyvinyl chloride has a durometer hardness in a range of approximately 60 to 80 Shore A.

19. The catheter introducer set of claim 18 wherein the polyvinyl chloride has a durometer hardness of approximately 70 Shore A.

* * * * *